(12) United States Patent
Yadid et al.

(10) Patent No.: US 7,652,191 B2
(45) Date of Patent: Jan. 26, 2010

(54) NONHUMAN MAMMALS EXHIBITING PTSD-LIKE BEHAVIOR

(75) Inventors: Gal Yadid, Shoham (IL); Joseph Zohar, Herzlia (IL)

(73) Assignee: Bar Ilan University, Ramat Gan (IL)

( * ) Notice: Subject to any disclaimer, the term of this patent is extended or adjusted under 35 U.S.C. 154(b) by 85 days.

(21) Appl. No.: 10/549,596

(22) PCT Filed: Mar. 18, 2004

(86) PCT No.: PCT/IL2004/000256

§ 371 (c)(1),
(2), (4) Date: May 30, 2006

(87) PCT Pub. No.: WO2004/082517

PCT Pub. Date: Sep. 30, 2004

(65) Prior Publication Data

US 2006/0225143 A1    Oct. 5, 2006

(51) Int. Cl.
*C12N 15/00*    (2006.01)
*A01K 67/033*    (2006.01)
*A01K 67/027*    (2006.01)

(52) U.S. Cl. .................. 800/21; 800/22; 800/9; 800/14

(58) Field of Classification Search .......... None
See application file for complete search history.

(56) References Cited

U.S. PATENT DOCUMENTS 6,486,198 B1    11/2002    Berlant
2005/0148650 A1    7/2005    Ohkawa

FOREIGN PATENT DOCUMENTS

WO    WO01/91548    12/2001
WO    WO03/074046    9/2003

OTHER PUBLICATIONS

Diamond et al. Exposing Rats to a Predator Impairs Spatial Working Memory in the Radial Arm Maze. Hippocampus. 1999, vol. 9, pp. 542-552.*
Cohen et al. Adminstration of High-Dose Ketoconazole, an Inhibitor of Steroid Synthesis Prevents Posttraumatic Anxiety in an Animal Model. European Neuropsychopharmacology. 2000, vol. 10, pp. 429-435.*
Adamec et al. NMDA Receptors Mediate Lasting Increases in Anxiety-Like Behavior Produced by the Stress of Predator Exposure—Implications for Anxiety Associated with Posttraumatic Stress Disorder. Physiology and Behavior. 1999, vol. 65, pp. 723-737.*
Posttraumatic stress disorder in the National Comorbidity Survey, Kessler et al; Arch Gen Psychiatry Dec. 1995; 52 (12): 1048-60.
Sertraline treatment of comorbid posttraumatic stress disorder and alcohol dependence. Brady et al; J Clin Psychiatry Dec. 1995; 56 (11): 502-5.
Pharmacotherapy for posttraumatic stress disorder. Stein et al Cochrane database Syst rev. 2000; (4): CD002795.
Hypothalamic-pituitary-adrenal dysfunction in posttraumatic stress disorder. Yehuda et al; Biol Psychiatry. Nov. 15, 1991; 30(10): 1031-48.
Twenty-four hour urinary cortisol and catecholamine excretion in combat-related posttraumatic stress disorder. Pitman et al; Biol Psychiatry Jan. 15, 1990; 27(2); 245-7.
Low urinary cortisol excretion in patients with posttraumatic stress disorder. Yehuda et al ; J Nerv Ment Dis. Jun. 1990; 178(6): 366-9.
Negative feedback regulation following administration of chronic exogenous corticosterone. Young et al; J Neuroendocrinol. Jan. 1995; 7(1): 37-45.
Substance abuse and schizophrenia: editors' introduction. Kosten et al; Schizophr Bull 1998; 24 (2):183.
The Relevance Of Differential Response To Trauma In An Animal Model Of Posttraumatic Stress Disorder. Cohen et al ; 2003 Society of Biological Psychiatry Mar. 15; 53(6): 463-73.
Diagnostic And Statistical Manual Of Mental Disorders, Fourth Edition, 2000, pp. 429, 463-648.
Nippon Shinkei Seishin Yakurigaku Zassi 114 (1): 43-49 Review Japanese, 1999.

* cited by examiner

*Primary Examiner*—Deborah Crouch
(74) *Attorney, Agent, or Firm*—Browdy and Neimark, PLLC

(57) ABSTRACT

The invention relates to production of maladapted animals characterized by PTSD like behavior from a population by behavioral conditioning. The method includes determining a baseline behavioral level for individual under defined conditions; exposing each individual animal to trauma event and further determining a posttraumatic event behavioral level; re-exposing each individual to a trauma related event and further determining an individual post trauma related event behavioral level and evaluating the individual post trauma related event behavioral level for each individual animal with respect to a baseline value according to a predetermined rule in order to determine which individuals are maladapted animals characterized by PTSD like behavior. Use of the method for assaying efficacy of PTSD treatment is within the scope of the invention, as are animals produced by claimed methods. Once the method is established, biological parameters may be employed in addition to, or in lieu of behavioral parameters.

18 Claims, 8 Drawing Sheets

Expression of Sigma receptor in the Amygdala

Expression of sigma receptor in the CA1

NONHUMAN MAMMALS EXHIBITING PTSD-LIKE BEHAVIOR

FIELD AND BACKGROUND OF THE INVENTION

The present invention relates to animals exhibiting PTSD like behavior, methods for production of same and methods for screening a candidate compound for PTSD treatment employing same and, more particularly, to a selected subset of non human animals which have been repeatedly exposed to a trauma.

Post-traumatic stress disorder (PTSD) is a common condition, which affects about 6% of the general population and has severe impact on the quality of life (Kessler et al., 1995). PTSD is an anxiety disorder that is developed by some individuals following the experience or witnessing of life-threatening events. PTSD is currently defined by the coexistence of three clusters of symptoms: re-experiencing, avoidance and hyper-arousal, which persist for at least one month, in survivors of a traumatic event (American Psychiatric Association, 1994).

The search for a safe and effective drug to treat of PTSD continues. Currently sertraline, a selective serotonin re-uptake inhibitor is approved for use in PTSD treatment full remission is not reported as a result of its use (Brady et al., 1995).

Abnormal activity of the autonomic nervous system (ANS) (Stein et al., 2000) and of the hypothalamic-pituitary-adrenal (HPA) axis (Yehuda et al. 1991) have been suggested as the basis of some of the characteristic behavioral features of PTSD. However, the findings concerning adrenocortical dysfunction in PTSD patients remain unclear. Pitman and Orr (1990) reported high 24-hour urinary cortisol in veterans with PTSD compared to normal controls with combat experience. Conversely, four studies reported lower 24-hour urinary cortisol in PTSD patients compared to normal controls, and to depressed patients (Yehuda et al. 1990). Young et al. (1995) reported enhanced pituitary proopiomelanocortin (POMC) messenger ribonucleic acid (mRNA) expression and corticotropin (ACTH) storage. Kosten et al. (1997) also reported elevated epinephrine level during PTSD patients as compared to major depressive disorder, paranoid schizophrenia and undifferentiated schizophrenia. As a result, there is no widely accepted biochemical parameter which could be used for rapid objective screening of the effect of a candidate compound on PTSD patients. This means that candidate compounds must be assayed on human PTSD patients followed by analysis of subjective evaluation of relief of behavioral symptoms.

While a number of animal models of PTSD have been suggested, none of these models address the well-accepted clinical findings that only a minority (about 20%) of individuals exposed to a traumatic event will eventually develop PTSD. For example, Cohen et al. (Biol Psychiatry. 2003 Mar. 15; 53(6):463-73), propose a model which relies upon a single 10-min exposure to a predator and arbitrarily selected cutoff behavioral criteria (CBC). This article makes no attempt to determine which animals will have a traumatic response when confronted with a stimulus related to the original trauma.

WO 200191548 teaches a transgenic animal model with a Wolfram Syndrome 1 (WFS1) transgene. The model is employed for evaluation of antidepressant drugs. This model has, an inherent disadvantage a strict dependence on a pre-selected biological parameter. Further, assay of efficacy of candidate compounds is neither taught nor fairly suggested. Further, a potential role for the Wolframin gene in PTSD is neither taught nor fairly suggested.

Similarly, while many candidate compounds for PTSD treatment such as PKB activators (see, for example, WO 03/074046), EP1 agonists (see, for example, WO 02/0765053), and topiramate and related sulfamates (see, for example, U.S. Pat. No. 6,486,198) are reported in the literature, reports of effective in vivo screening are less frequent owing to the absence of a reliable animal model. Thus, there is a strong possibility that a known compound has potential utility in treatment of PTSD but that the difficulty associated with screening of candidate compounds will preclude its "discovery" as a PTSD treatment.

There is thus a widely recognized need for, and it would be highly advantageous to have, animals exhibiting PTSD like behavior, methods for production of same and methods for screening a candidate compound for PTSD treatment employing same devoid of the above limitation(s).

SUMMARY OF THE INVENTION

According to one aspect of the present invention there is provided a maladapted non-human animal conditioned to exhibit at least one PTSD like behavior selected from the group consisting of: (a) re-experiencing a trauma in response to a stimulus associated with the trauma, (b) avoidance of social interaction; and (c) hyper-arousal in response to a stimulus not associated with the trauma.

According to another aspect of the present invention there is provided a method for producing a small group of maladapted non-human animals characterized by PTSD like behavior from a larger group of animals by behavioral conditioning. The method includes: (a) determining an individual baseline behavioral level for each one of an individual animal in the larger group after a period of habituation to a defined set of conditions; (b) exposing each one of the individual animal in the larger group to a trauma event and further determining an individual posttraumatic event behavioral level for each of the individual animal; (d) re-exposing each of the individual animal in the larger group to a trauma related event and further determining an individual post trauma related event behavioral level for each individual animal; (e) evaluating the individual post trauma related event behavioral level for each individual animal with respect to at least one baseline value according to a predetermined rule in order to determine which of said individual animal in the larger group belong to the small group of maladapted animals characterized by PTSD like behavior.

According to yet another aspect of the present invention there is provided a method for screening a candidate compound for PTSD treatment. The method includes: (a) producing a small group of individually evaluated maladapted non-human animals characterized by PTSD like behavior from a larger group of animals wherein an individual in the small group is correlatable to a corresponding individual behavioral profile; (b) identifying each of the individuals in the small group of individually evaluated maladapted non-human animals characterized by PTSD like behavior; (c) administering a candidate compound to at least a portion of the individuals in the small group; and (d) determining an effect of the candidate compound on each of the individuals in the at least a portion of the small group with respect to the corresponding individual behavioral profile.

According to a further additional aspect of the present invention there is provided a method for screening a candidate compound for prophylactic PTSD treatment. The method includes: (a) establishing a method for producing a small group of maladapted non-human animals characterized by PTSD like behavior from a large group of animals by behavioral conditioning; (b) employing statistical methods to determine a confidence interval for a relative size of the small group of maladapted non-human animals characterized by PTSD like behavior with respect to a size of the large group of animals; (c) administering the candidate compound to a subsequent large group of animals subjected to the method for producing a subsequent small group of maladapted non-human animals characterized by PTSD like behavior; and (d) determining whether a relative size of the subsequent small group of maladapted non-human animals characterized by PTSD like behavior with respect to a size of the subsequent large group of animals falls within the confidence interval.

According to yet another aspect of the invention, there is provided a method for screening a candidate compound for PTSD treatment. The method includes: (a) establishing a method for producing a small group of maladapted PTSD like non-human animals from a large group of animals by behavioral conditioning; (b) measuring at least one biological parameter for each animal in the small group of maladapted PTSD like non-human animals; (c) employing statistical methods to (i) determine a first confidence interval for a relative size of the small group of maladapted PTSD like non-human animals with respect to a size of the large group of animals and (ii) determine a second confidence interval for the at least one biological parameter for the small group of maladapted PTSD like non-human animals; (d) administering the candidate compound to a subsequent large group of animals subjected to the method for producing a subsequent small group of maladapted non-human animals characterized by PTSD like behavior; and (e) determining whether a relative size of a subset of the subsequent large group of animals characterized by a value for the at least one biological parameter which falls within the second confidence interval falls within the first confidence interval; and (f) concluding that: (i) the candidate compound is effective in ameliorating PTSD if the relative size of the subset of the subsequent large group of animals characterized by a value for the at least one biological parameter which falls within the second confidence interval is below a lower bound of the first confidence interval; or (ii) the candidate compound is not effective in ameliorating PTSD if the relative size of the subset of the subsequent large group of animals characterized by a value for the at least one biological parameter which falls within the second confidence interval is above a lower bound of the first confidence interval.

According to further features in preferred embodiments of the invention described below, the maladapted non-human animal is further characterized by a change in at least one biological parameter.

According to still further features in the described preferred embodiments the at least one biological parameter is selected from the group consisting of a Wolframin level and a Sigma 1 receptor level.

According to still further features in the described preferred embodiments maladapted non-human animal is characterized by at least two of the PTSD like behaviors.

According to still further features in the described preferred embodiments the maladapted non-human is characterized by all three of said PTSD like behaviors.

According to still further features in the described preferred embodiments the baseline value is selected from the group consisting of: (i) the individual baseline behavioral level for an animal which is a subject of the individual post trauma related event behavioral level; (ii) the individual post traumatic event behavioral level for the animal which is a subject of said individual post trauma related event; (iii) an upper limit of a range of a pool of values of the individual baseline behavioral level for each one of an individual animal in the larger group; (iv) a mean average of the range of a pool of values of the individual baseline behavioral level for each one of an individual animal in the larger group; and (v) a mode average of the range of a pool of values of the individual baseline behavioral level for each one of an individual animal in the larger group.

According to still further features in the described preferred embodiments the determining of an individual baseline behavioral level, the further determining of an individual post traumatic event behavioral level, the further determining of al individual post trauma related event behavioral level are each independently accomplished by analysis of videotapes of a defined behavior of the individual animal under controlled conditions.

According to still further features in the described preferred embodiments the defined behavior of the individual animal is freezing.

According to still further features in the described preferred embodiments the controlled conditions include at least one set of conditions selected from the group consisting of the individual animal alone the individual animal together with a habituated companion animal and the individual animal exposed to a stimulus not related to the trauma event.

According to still further features in the described preferred embodiments the method further includes at least one repetition of the re-exposing each of the individual animal in the larger group to a trauma related event and of the further determining an individual post trauma related event behavioral level for each individual animal.

According to still further features in the described preferred embodiments the method further includes evaluating an ability of a candidate compound to cause a behavioral level of an individual maladapted animal treated with the candidate compound to revert towards the baseline.

According to still further features in the described preferred embodiments a maladapted non-human animal produced and identified according to the method is provided.

According to still further features in the described preferred embodiments the method further includes applying an accepted statistical analysis to a pool of data pertaining to the effect of the candidate compound on each of the individuals in the at least a portion of the small group with respect to the corresponding individual behavioral profile.

According to still further features in the described preferred embodiments the method further includes administering a control compound to an additional at least at least a portion of the individuals in the small group.

According to still further features in the described preferred embodiments the control compound includes at least one compound selected from the group consisting of a negative control compound and a compound with a previously characterized efficacy in treating PTSD.

According to still further features in the described preferred embodiments the method is performed as iterated and the treatment is a therapeutic treatment.

According to still further features in the described preferred embodiments the treatment is a prophylactic treatment.

The present invention successfully addresses the shortcomings of the presently known configurations by providing maladapted animals characterized by PTSD like behavior and methods of producing same. The maladapted animals serve as a models system for evaluation of compounds which are candidates for use in treatment of PTSD.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
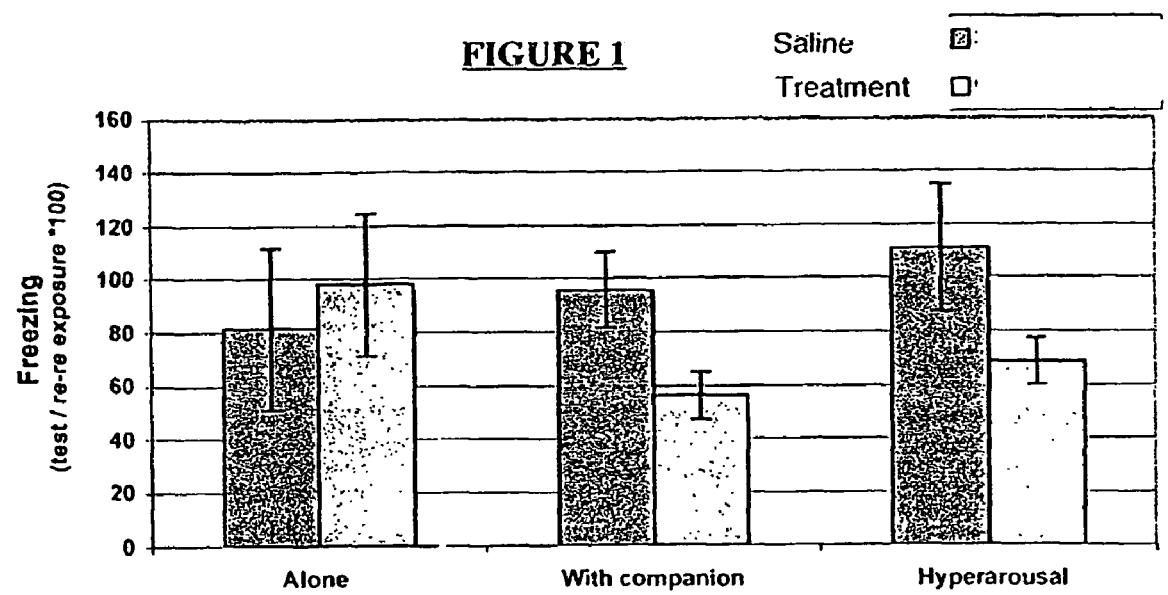
FIG. 1 is a comparative bar graph illustrating normalized values for freezing behavior in rats in rats treated with saline (n=11) or candidate compound (n=16) for 14 days in the three conditions separately. The magnitude of changes in freezing (normalized values) was determined by dividing the percent of total time freezing during the test (after 14 days of treatment) by the percent of total time freezing in the re-re-exposure (before treatment). Decreased values indicate improvements in freezing behavior. The mean of normalized freezing values±sem are presented ($p<0.05$).

The present invention is of methods for production of animals exhibiting PTSD like behavior and of the PTSD like animals produced by these methods. These methods and/or animals can be employed in screening candidate compounds for PTSD treatment. Specifically, the present invention can be used to determine efficacy of a candidate compound with respect to defined behavioral and/or biological parameters associated with PTSD.

The principles of methods and use of animals according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The invention is most concretely embodied by a maladapted non-human animal conditioned to exhibit at least one, more preferably two or more, most preferably three or more PTSD like behavior(s). A PTSD like behavior may be, for example, re-experiencing a trauma in response to a stimulus associated with the trauma, or avoidance of social interaction, or hyper-arousal in response to a stimulus not associated with the trauma. Examples presented hereinbelow establish that these maladapted non-human animals may be further characterized by a change in at least one biological parameter such as, for example, a Wolframin mRNA expression level and/or a Sigma 1 receptor level mRNA expression. It is anticipated that following disclosure of the animal model described herein, additional relevant biological parameters will be characterized and these are included a priori.

A method for producing a small group of maladapted non-human animals characterized by PTSD like behavior from a larger group of animals by behavioral conditioning constitutes an additional embodiment of the invention. The method includes determining an individual baseline behavioral level for each individual animal in the larger group after a period of habituation to a defined set of conditions. The method further includes exposing each individual animal in the larger group to a trauma event and further determining an individual post-traumatic event behavioral level for each individual animal.

The method further includes re-exposing each individual animal in the larger group to a trauma related event and further determining an individual post trauma related event behavioral level for each individual animal.

The method further includes evaluating the individual post trauma related event behavioral level for each individual animal with respect to at least one baseline value according to a predetermined rule in order to determine which of said individual animal in the larger group belong to the small group of maladapted animals characterized by PTSD like behavior.

The evaluation may be performed with respect to, for example, the individual baseline behavioral level for the animal which is the subject of the individual post trauma related event behavioral level.

Alternately, but also preferably, the evaluation may be performed with respect to, the individual post traumatic event behavioral level for the animal which is the subject of the individual post trauma related event.

According to one especially preferred embodiment, the evaluation may be performed with respect to, an upper limit of a range of a pool of values of the individual baseline behavioral level for each one of an individual animal in the larger group.

According to another especially preferred embodiment, the evaluation may be performed with respect to, a mean average of the range of a pool of values of said individual baseline behavioral level for each one of an individual animal in the larger group. Alternately, but also preferably, a mode average may be employed in place of a mean average.

Whatever the basis for comparison, the evaluation is performed according to a predetermined rule. The evaluation determines, for each animal, whether it belongs to the small group of maladapted animals characterized by PTSD like behavior.

Optionally, but preferably, the method further includes measuring at least one biological parameter affected by the behavioral conditioning as detailed hereinabove and hereinbelow.

One means for determining an individual baseline behavioral level, an individual post traumatic event behavioral level, and an individual post trauma related event behavioral level is by analysis of stored visual records (e.g. videotapes) of a defined behavior of the individual animal under controlled conditions. However, alternative methods such as the use of the "Startle Reflex System" (San Diego Instruments, San Diego, Calif.) or similar device may obviate the need for visual observation. The exact means employed for determination will not affect practice of the disclosed method, or the PTSD animals produced thereby, to any significant degree.

According to a most preferred embodiment of the invention, the defined behavior of the individual animal is freezing. For purposes of this specification and the accompanying claims, "freezing" is defined as any perceptible cessation of motion. While the amount of freezing measured may vary slightly depending upon the determination method employed, the overal outcome should be uniformly reliable so long as the same determination method is employed throughout a study.

Controlled conditions may include, but are not limited to, the individual animal alone, the individual animal together with a habituated companion animal and the individual animal exposed to a stimulus not related to the trauma event.

Optionally, but preferably, the method further includes at least one repetition of the re-exposing each of the individual animals in the larger group to a trauma related event and of the further determining an individual post trauma related event behavioral level for the individual animal.

According to a most preferred embodiment of the invention, the method further serves as a vehicle for evaluating an ability of a candidate compound to cause a behavioral level of an individual maladapted animal treated with the candidate compound to revert towards a baseline behavioral level of the animal.

Any maladapted non-human animal produced and identified according to the method constitutes an integral part of the invention.

The invention is further embodied by a method for screening a candidate compound for PTSD treatment. The method includes producing a small group of individually evaluated maladapted non-human animals characterized by PTSD like behavior from a larger group of animals wherein an individual in the small group is correlatable to a corresponding individual behavioral profile The method further includes identifying each of the individuals in the small group of individually evaluated maladapted non-human animals characterized by PTSD like behavior and administering a candidate compound to at least a portion of the individuals in the small group.

The method further includes determining an effect of the candidate compound on each of the individuals in the at least a portion of the small group with respect to the corresponding individual behavioral profile.

Most preferably, the method further includes measuring at least one biological parameter in each of the individually evaluated maladapted non-human animals as detailed hereinbelow and hereinabove.

Practice of the method may further include applying an accepted statistical analysis to a pool of data pertaining to the effect of the candidate compound on each of the individuals in the at least a portion of the small group with respect to the corresponding individual behavioral profile.

In order to increase the predictive value of the method, it may be desirable to administer a control compound to an additional at least at least a portion of the individuals in the small group. The control compound may be, according to various preferred embodiments of the method, a negative control compound or a compound with a previously characterized efficacy in treating PTSD. Most preferably, both types of control compounds are employed.

According to one preferred embodiment of the invention the method is performed as iterated hereinabove and the candidate compound is a candidate for therapeutic treatment.

According to still further features in the described preferred embodiments the method is performed as iterated, although not necessarily in the iterated order, and the candidate compound is a candidate for prophylactic treatment.

According to a further additional aspect of the present invention there is provided a method for screening a candidate compound for prophylactic PTSD treatment. The method includes establishing a method for producing a small group of maladapted non-human animals characterized by PTSD like behavior from a large group of animals by behavioral conditioning.

The method further includes employing statistical methods to determine a confidence interval for a relative size of the small group of maladapted non-human animals characterized by PTSD like behavior with respect to the size of the large group of animals screened.

The method further includes administering the candidate compound to a subsequent large group of animals subjected to the method for producing a subsequent small group of maladapted non-human animals characterized by PTSD like behavior and determining whether a relative size of the subsequent small group of maladapted non-human animals characterized by PTSD like behavior with respect to a size of the subsequent large group of animals falls within the confidence interval.

Once the behavioral model is established an a well correlated biological parameter has been identified and characterized, it is feasible to substitute biological measurements for behavioral measurements as detailed hereinbelow in Example 17. On other words, the invention is further embodied by a method for screening a candidate compound for PTSD treatment. The method includes: establishing a method for producing a small group of maladapted PTSD like non-human animals from a large group of animals by behavioral conditioning as detailed hereinabove and hereinbelow. The method further includes measuring at least one biological parameter for each animal in the small group of maladapted PTSD like non-human animals. As detailed hereinabove and hereinbelow, the biological parameter may be, for example, a Wolframin expression level or a Sigma 1 receptor expression level. The method further includes employing statistical methods to determine a first and a second confidence interval.

The first confidence interval defines a relative size of the small group of maladapted PTSD like non-human animals with respect to a size of the large group of animals.

The second confidence interval defines a range of values for the at least one biological parameter which serve to indicate membership in the small group of maladapted PTSD like non-human animals.

Once these two confidence intervals are rteliably defined, an investigator may proceed to administer the candidate compound to a subsequent large group of animals. The animals in this subsequent large group are subjected to the method for producing a subsequent small group of maladapted non-human animals characterized by PTSD like behavior as described hereinabove and hereinbelow. It should be noted that administration of the candidate compound may occur before, during oir after the behavioral conditioning.

The method further includes determining whether a relative size of a subset of the subsequent large group of animals characterized by a value for the at least one biological parameter which falls within the second confidence interval falls within the first confidence interval.

If the relative size of the subset of the subsequent large group of animals characterized by a value for the at least one biological parameter which falls within the second confidence interval is below a lower bound of the first confidence intervaland it is indicative that the candidate compound is effective in ameliorating PTSD.

If the relative size of the subset of the subsequent large group of animals characterized by a value for the at least one biological parameter which falls within the second confidence interval is above a lower bound of the first confidence interval it is indicative that the candidate compound is not effective in ameliorating PTSD.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Before presesnting examples, reference is made to the following materials and methods employed in performance of experiments described in the examples.

Materials and Methods:

Animals: Adult, male Sprague-Dawley rats (250-300 g; Harlan, Israel) were used throughout the described study. The animals were housed 3 per cage under conditions of constant temperature (22° C.) and 50% humidity, with a 12-hour light, 12-hour dark cycle. Every two tested rats were housed with a third companion rat (one) in a cage. The same 3 rats remained together until the end of the study. Food and water was provided ad libitum. Animals were allowed to becom familiar with the housing conditions of Bar-Ilan University for 10 days before experiments began. All animal procedures were approved by the Bar-Ilan University Animal Care Committee and were carried out in accordance with the NIH Guide for the Care and Use of Laboratory Animals.

Figure 12:
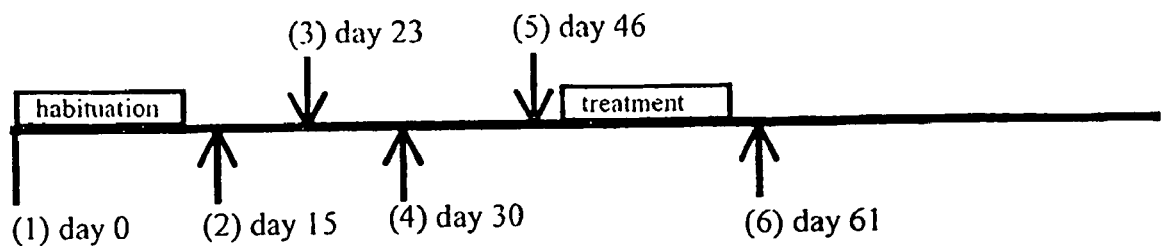
FIG. 12 is timeline indicating the temporal relationship of important events in the described animal Study.

Habituation: Rats were initially habituated to the open field with their cage companion for 14 days, 5 min per day (see FIG. 12). The open field was 90×90×30 cm poligal (plastic polimer) box which was placed under a camera to fcilitate bahavioral measurements.

Behavioral measurements: After each exposure to trauma or trauma related stimulus, freezing time was monitored (videotaped) using an observer apparatus (Noldus, The Netherlands). Freezing time was monitored sequentially while the subject rat was; (a) alone (5 minutes), (b) with its habituated companion rat (5 minutes), and (c) after a hyper-arousal event (5 minutes). The "hyper-arousal" event was a loud recorded drumbeat played back to the tested rats in each "hyper-arousal" observation period. The subject rat was not removed from the open field or touched during the series of 3 behavioral measurements (a,b and c). The set of three behavioral measurements were conducted consecutively in the same open-field. The freezing time was expressed as a percent (%) of total time (see results presented hereinbelow). All measurements were performed during the day between 8:00 and 14:00 hours in daylight. The video and computer equipment were situated in a separate room and all video and observation analysis were done in that room.

Determination of Baseline: Baseline behavioral parameters were measured under three separate conditions on day 15 without exposure to any trauma related environmental cues (i.e. litter or cat scent; see FIG. 12 item 2). Baseline readings were recorded for each individual animal, although in some cases the range of baseline values was compared to a subsequent measurement of an individual animal Initial exposure to trauma: One week after the end of habituation (day 23 see FIG. 12 item 3), rats were exposed to litter with a cat scent for 30 min. and tested for behavior under three separate conditions. Initial trauma exposure, in the form of cat scent exposure was performed in a different room from that employed for subsequent behavioral testing. The freshly soiled cat litter (litter which the cat used in the 24 hours before the experiment) was spread in a clean plastic cylinder, and each tested rat was exposed individually when placed in that cylinder for 30 min. before the test in the open field. The cylinder was cleaned between use by each individual rat in order to prevent additional signals of rat origin from confounding the experiment. Freshly soiled litter from the same cat was used through the study. The temperature and humidity conditions in the trauma exposure area were identical to the housing and behavioral testing area conditions. The group of-rats which were not exposed to the trauma were housed in separate cages in a separate housing area throughout the experiment. This untraumatized group was always the first to be examined in each study group and were tested before the traumatized rats (on a separate day). The untraumatized control group was exposed in an identical cylinder for 30 min. to the same amount of clean litter (i.e. without cat scent). The open field employed for behavioral monitoring of rats was cleaned between each tested rat in order to prevent additional signals of rat origin from confounding the experiment.

Initial re-exposure to trauma related stimulus: One week following the initial exposure to actual trauma (day 30; see FIG. 12 item 4), rats were re-exposed for 30 minutes to clean litter with the same texture but without a cat scent and subjected to behavior monitoring under three separate conditions.

Subsequent re-exposure trauma related stimulus: Four weeks after the initial exposure (46 days; see FIG. 12 item 5.), rats were again exposed to litter with the same texture, but without the cat scent. Immediately after this exposure, they were subjected to behavior monitoring under three separate conditions and then defined as maladapted (PTSD) or non-maladapted rats based on results of those behavioral observations.

Data analysis: The range of each measured behavioral parameter was determined for each experimental group after habituation. The upper and lower levels of this range were treated as the "normal baseline" and alterations from this range were used to define PTSD. If a trend of increased freezing over time was observed but the values still did not exceed the upper level of the "normal baseline", the rat was defined as "border-line". In the data presented hgereinbelow, only those rats which were above the baseline range under all three behavioral conditions were deined as PTSD.

Treatment: Beginning the following day (day 47; see FIG. 12), maladapted rats were administered a candidate compound (20 mg/kg/day) or saline for 14 days using Alzet osmotic pumps. The observer and experimenter were blinded to the treatment.

Measurement to determine treatment efficacy: At the completion of the 14 days of candidate compound or saline treatment (Day 61; see FIG. 12 item 6)., the rats were re-tested in the open field for behavioral performance in the three conditions.

Brain mRNA analysis: After completion of the behavioral study, rats without treatment were sacrificed and Brain Amygdala and CA were collected by biopsy. Using commercially avaialable reagents, mRNA was prepared. Northern blots were prepared and probed with specific probes as appropriate using standard molecular biology techniques ("Molecular Cloning: A laboratory Manual" Sambrook et al., (1989); "Current Protocols in Molecular Biology" Volumes I-III Ausubel, R. M., ed. (1994)).

Example 1

Selection of a Behavior for Use as an Indicator of Stress

In order to determine what behavior might be reliably used as an indicator of stress a preliminary experiment was conducted. In the preliminary study, freezing, grooming, sniffing, climbing over, staying in the corner, crawling under, and genital investigation were measured. After an initial analysis of the above parameters, we concluded that the freezing parameter was the only parameter that was significantly different between maladapted and non-maladapted rats.

TABLE 1

Summary of observations of various behaviors for rats observed "alone" without trauma (normal range), in response to trauma, and for maladapted PTSD animals. (results expressed as % of total time)

| Observed behavior | Normal range | Trauma | PTSD[A] |
|---|---|---|---|
| Freezing | 0-8 | 0-30 | 12-70 |
| Grooming | 7-13 | 3-28 | 4-13 |
| Sniffing | 6-14 | 3-30 | 11-22 |

TABLE 1-continued

Summary of observations of various behaviors for rats observed "alone" without trauma (normal range), in response to trauma, and for maladapted PTSD animals. (results expressed as % of total time)

| Observed behavior | Normal range | Trauma | PTSD[A] |
|---|---|---|---|
| Climbing over | 12-17 | 3-27 | 2-4 |
| Staying in the corner | 29-43 | 14-75 | 51-75 |

[A]PTSD group are those rats absolutely above normal range after a second re-exposure to a trauma like stimulus.

TABLE 2

Summary of observations of various behaviors for rats observed "with companion" without trauma (normal range), in response to trauma, and for maladapted PTSD animals. (results expressed as % of total time)

| Observed behavior | Normal | Trauma | PTSD[A] |
|---|---|---|---|
| Freezing | 0-6 | 0-20 | 10-40 |
| Grooming | 11-17 | 0-4 | 0-2 |
| Sniffing | 8-16 | 0-42 | 26-42 |
| Climbing over | 6-12 | 5-46 | 7-13 |
| Crawling under | 0-2 | 0-19 | 2-4 |
| Genital investigation | 0-2 | 0-28 | 0-2 |
| Staying in the corner | 23-37 | 0-45 | 25-45 |

[A]PTSD group are those rats absolutely above normal range after a second re-exposure to a trauma like stimulus.

TABLE 3

Summary of observations of various behaviors for rats observed "after hyperarousal" (exposure to a stimulus not related to trauma) without trauma (normal range), in response to trauma, and for maladapted PTSD animals. (results expressed as % of total time)

| Observed behavior | Normal | Trauma | PTSD |
|---|---|---|---|
| Freezing | 0-20 | 5-30 | 30-70 |

[A] PTSD group are those rats absolutely above normal range after a second re-exposure to a trauma like stimulus.

Base upon results summarized in tables 1 and 2, freezing was chosen as a suitable behavior to identify PTSD like behavior in the "alone" and "with companion" situations. Results summarized in table 3 confirmed that freezing is also suited for use in identification of PTSD like behavior in the hyperarousal situation. Statistical analysis was by the T-test for normal distribution throughout.

Example 2

Identification of Maladapted Rats

Subsequent to selection of freezing behavior as a reliable indication of PTSD like behavior, an experiment was conducted to identify a subset of maladapted animals from within a larger group. To that end four study groups (1-4) of rats were tested (total 147 rats), an addition four control groups (total 31 rats) were tested according to the protocol detailed herinabove in "Materials and Methods" and summarized graphically in FIG. 12. Results from these experiments are summarized in table 4. The significant and border-line maladapted rats in each group were selected after exhibiting a behavioral profile, as manifested by freezing behavior under three sets of conditions, that is consistent with human PTSD.

Briefly, for group 1 the upper level for the normal baseline expressed as % of total time was 8.1 in the alone condition, 6 in the with companion condition and 21.8 in the hyperarousal condition. In group 1 a total of ten rats were defined as maladapted (above the upper level in all 3 conditions):

Briefly, for group 2 the upper level for the normal baseline expressed as % of total time was 8.7 in the alone condition, 5.2 in the with companion condition and 20.5 in the hyperarousal condition. In group 2 a total of three rats were defined as maladapted (above the upper level in all 3 conditions). A single unexposed rat from group 2 met the criteria for maladapted. This unexpected observation, although it remains unexplained, does not detract from the value or utility of the described PTSD model.

Briefly, for group 3 the upper level for the normal baseline expressed as % of total time was 9.3 in the alone condition, 12.1 in the with companion condition and 24.8 in the hyperarousal condition. In group 3 a total of four rats were defined as maladapted (above the upper level in all 3 conditions). A single unexposed rat from group 3 met the criteria for maladapted. Again, although this unexpected observation remains unexplained, it does not detract from the value or utility of the described PTSD model.

Briefly, for group 4 the upper level for the normal baseline expressed as % of total time was 14.4 in the alone condition, 5.7 in the with companion condition and 28.2 in the hyperarousal condition. In group 4 a total of ten rats were defined as maladapted (above the upper level).

TABLE 4

Summary of results from identification of maladapted (PTSD) rats

| group number | unexposed animals | Exposed animals | Significant maladapted (PTSD) | Border-line maladapted (PTSD) | Total maladapted (PTSD) | PTSD/exposed (%) |
|---|---|---|---|---|---|---|
| 1 | 8 | 28 | 7 | 3 | 10 | 35.71% |
| 2[A] | 8 | 28 | 3 | 0 | 3 | 10.71% |
| 3[A] | 8 | 27 | 2 | 2 | 4 | 14.81% |
| 4 | 7 | 33 | 6 | 4 | 10 | 30.3% |
| Total | 31 | 116 | 18 | 9 | 27 | 23.2% |

[A]one maladapted rat was identified among unexposed animals in this group

Example 3

Testing of a Candidate Compound for PTSD Treatment Efficacy on Previously Identified Maladapted Rats Maladapted (PTSD) rats identified in the experiment described in example 2 were assigned to either a treatment (candidate compound) or control (saline) group (table 5). A total of 16 rats were treated with candidate compound and a total of 11 rats were treated served as controls and were injected with saline. Treatment and behavioral observations were as detailed hereinabove in Methods and Materials and depicted graphically in FIG. 12.

Various assessments of the efficacy of treatment are described below and summarized in FIGS. 1 through 11.

TABLE 5

Grouping of maladapted rats for testing of candidate compound

| group number | # treat. | Ind. ID # | # control | Ind. ID # | Total/ group |
|---|---|---|---|---|---|
| 1 | 5 | 12, 18, 19, 20, 35 | 5 | 14, 22, 23, 25, 32 | 10 |
| 2 | 2 | 26, 33 | 1 | 31 | 3 |
| 3 | 3 | 26, 27, 33 | 1 | 31 | 4 |
| 4 | 6 | 13, 18, 26, 27, 29, 39 | 4 | 17, 19, 28, 38 | 10 |
| Total | 16 | NA | 11 | NA | 27 |

Example 4

Analysis of Freezing Behaviour under Three Separate Sets of Controlled Conditions Changes in freezing behavior (normalized values) in rats treated with saline (dark grey bars) or candidate compound (light grey bars) as described in example 3 either alone, with companion, or under hyperarousal conditions are presented separately. The magnitude of changes in freezing (normalized values) was determined by dividing the percent of total time freezing during the test (after 14 days of treatment) by the percent of total time freezing in the re-re-exposure (before treatment). Decreased values indicate improvements in freezing behavior for the specific animal measured relative to its own previous behavior. The mean of normalized freezing values±SEM are presented graphically in FIG. 1 ($p<0.05$). Statistical analysis was a T-test normal distribution. The Star indicates significance. These results indicate that the assayed candidate compound is contraindicated for patients with re-experiencing symptoms but may be indicated for relief of problems with social interaction and/or exaggerated startle response.

Example 5

Figure 2:
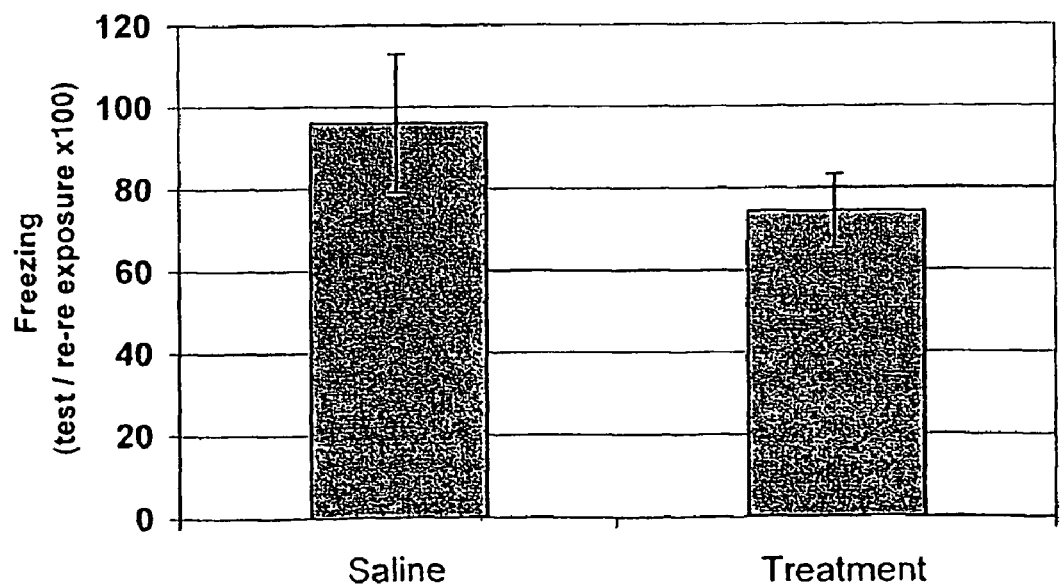
FIG. 2 is a comparative bar graph illustrating changes in freezing (normalized values) in rats treated with saline (n=11) or candidate compound (n=16) for 14 days in all three conditions together. The magnitude of changes in freezing was computed as in FIG. 1. Decreased values indicate improvements in freezing behavior. The mean of normalized freezing values±sem are presented ($p<0.05$).
Figure 3:
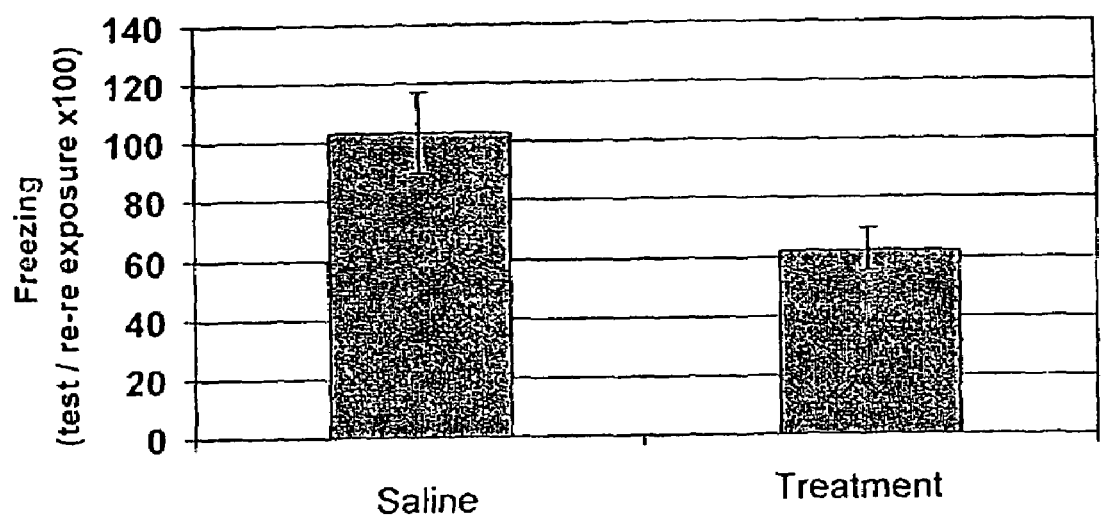
FIG. 3 is a is a comparative bar graph illustrating changes in freezing (normalized values) in rats treated with saline (n=11) or candidate compound (n=16) for 14 days in two conditions ("with companion" and "hyper-arousal"). The magnitude of changes in freezing was computed as in FIG. 1. Decreased values indicate improvements in freezing behavior. The mean of normalized freezing values±sem are presented ($p<0.05$).
Figure 4:
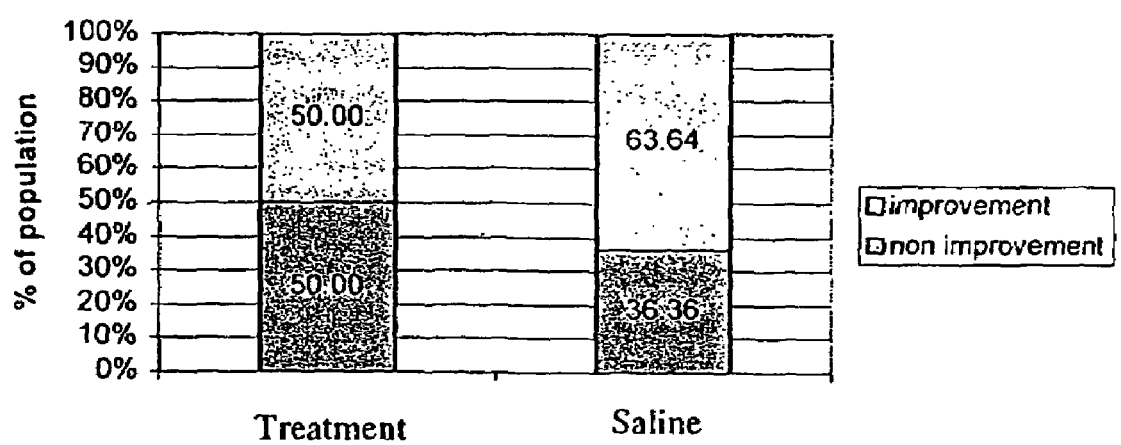
FIG. 4 is a split bar graph illustrating the breakdown of the population of saline-(n=11) and candidate compound-treated (n=16) rats that improved or did not improve above 30% after treatment in the "alone" condition.
Figure 5:
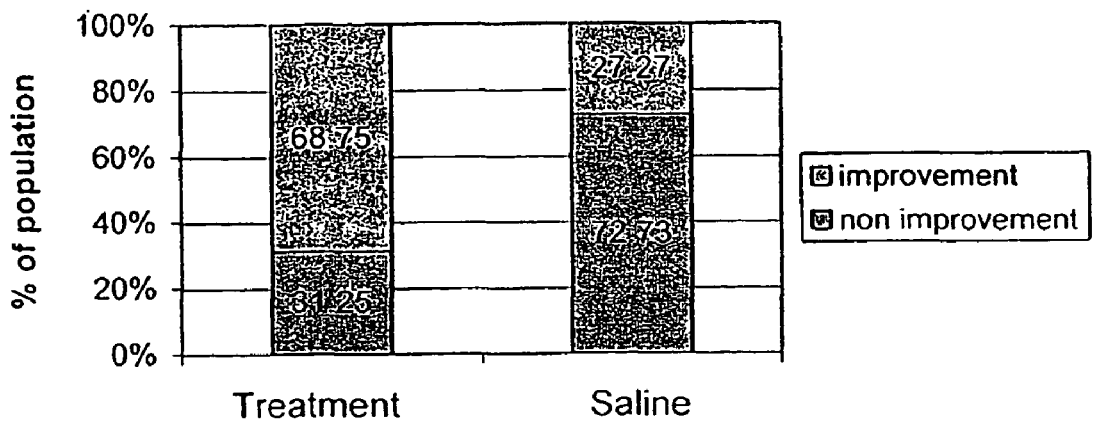
FIG. 5 is a split bar graph illustrating the breakdown of the population of saline-(n=11) and candidate compound-treated (n=16) rats that improved or did not improve above 30% after treatment in the avoidance "with companion" condition.

Analysis of Freezing Behaviour under Three Sets of Controlled Conditions Analyzed as a Pool Changes in freezing (normalized values) in rats treated with saline or candidate compound as described in example 3 in all three conditions together were pooled and are summarized graphically in FIG. 2. The magnitude of changes in freezing (normalized values) was determined as described hereinabove. Decreased values indicate improvements in freezing behavior for the specific animal measured relative to its own previous behavior. The mean of normalized freezing values±SEM are presented ($p<0.05$). Statistical analysis was as in Example 4.

Example 6

Analysis of Freezing Behaviour under Two Sets of Controlled Conditions Analyzed as a Pool Changes in freezing (normalized values) in rats treated with saline or candidate compound as described in example 3 under conditions of with companion and hyper-arousal were pooled while results under alone conditions were excluded. Results are summarized graphically in FIG. 3. The magnitude of changes in freezing (normalized values) was determined by dividing the percent of total time freezing during the test (after 14 days of treatment) by the percent of total time freezing in the re-re-exposure (before treatment). Decreased values indicate improvements in freezing behavior for the specific animal measured relative to its own previous behavior. The mean of normalized freezing values±SEM are presented ($p<0.05$). Statistical analysis was as in Example 4.

Inclusion of the alone condition served to describe the individual re-experiencing of the trauma.

Example 7

Analysis of 30% Amelioration of Symptoms under with Companion Conditions

In order to more easily assess the efficacy of the candidate compound, a 30% improvement as a result of treatment was chosen as a threshold. The percentage saline-treated and candidate compound-treated rats that improved (light grey portion of bar) or did not improve (dark grey portion of bar) by more than 30% as a result of treatment in the avoidance "with companion" condition is summarized graphically in FIG. 5. The candidate compound more than doubled the number of animals experiencing a 30% improvement indicating that it has potential utility in ameliorating problems with social interaction in human PTSD patients. Statistical analysis was as in Example 4, Results were significant ($p<0.05$).

Example 8

Analysis of 30% Amelioration of Symptoms under Hyper Arousal Conditions

Figure 6:
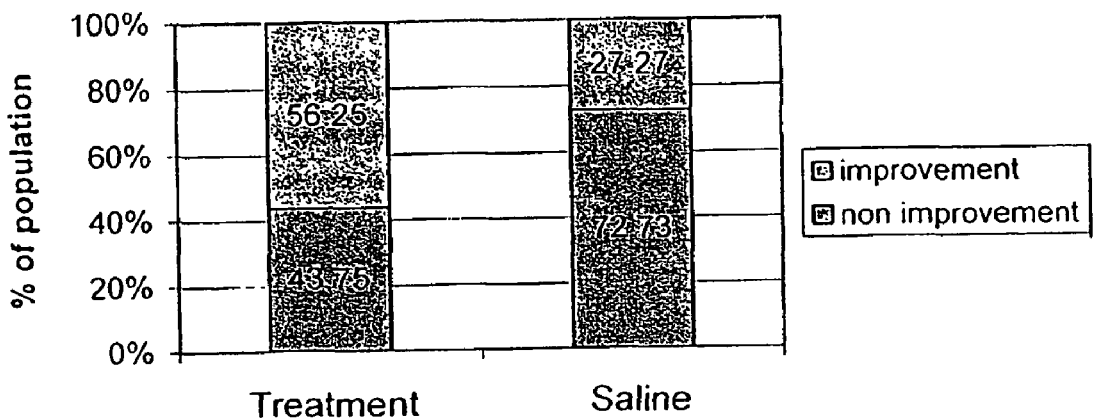
FIG. 6 is a split bar graph illustrating the breakdown of the population of saline-(n=11) and candidate compound-treated (n=16) rats that improved or did not improve above 30% after treatment in the "hyper-arousal" condition.
Figure 7:
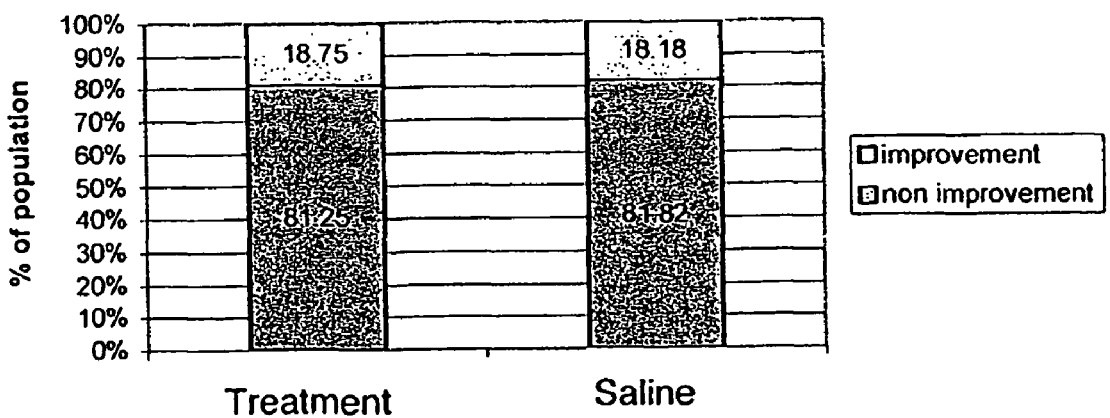
FIG. 7 is a split bar graph illustrating the breakdown of the population of saline-(n=11) and candidate compound-treated (n=16) rats that improved or did not improve above 30% after treatment in the all three monitoring situtations together.
Figure 8:
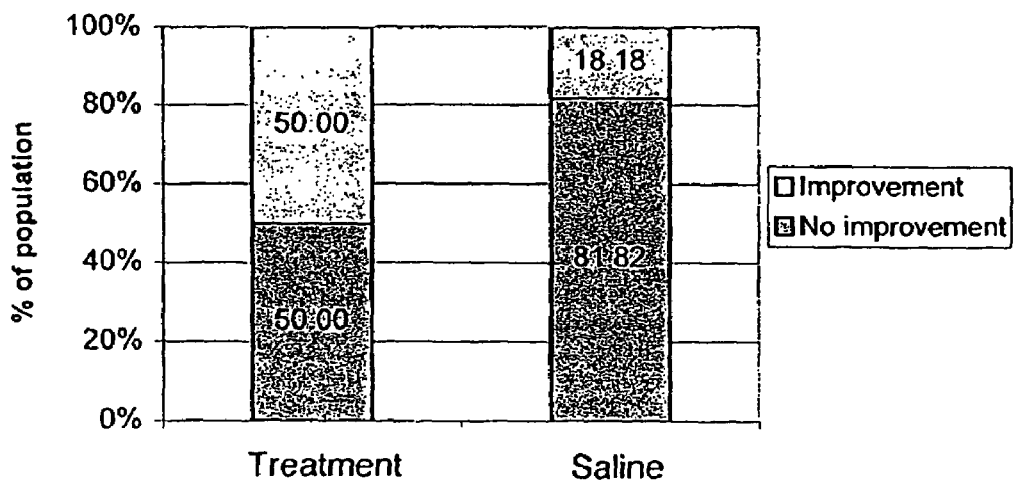
FIG. 8 is a split bar graph illustrating the breakdown of the population of saline-(n=11) and candidate compound-treated (n=16) rats that improved or did not improve above 30% after treatment in avoidance "with companion" and "hyper-arousal" conditions combined

Using the same 30% improvement threshold described in example 7, the percentage of saline-treated and candidate compound-treated rats that improved (light grey portion of bar) or did not improve (dark grey portion of bar) as a result of treatment under hyper arousal conditions was analyzed Results are summarized graphically in FIG. 6. Again, the candidate compound more than doubled the number of animals experiencing a 30% improvement indicating that it has potential utility in ameliorating problems with amplified startle response in human PTSD patients. Statistical analysis was as in Example 4, Results were significant ($p<0.05$).

Example 9

Analysis of 30% Amelioration of Symptoms with Three Sets of Conditions Analyzed as a Pool Using the same 30% improvement threshold described in example 7, the percentage of saline-treated and candidate compound-treated rats that improved (light grey portion of bar) or did not improve (dark grey portion of bar) as a result of treatment under hyper arousal conditions was analyzed. Results are summarized graphically in FIG. 7. In this case, the candidate compound had no significant effect on the number of animals experiencing a 30% overall improvement in the face of the three sets of test conditions. This lack of overall effect may be attributed to the adverse effect of the test compound in the alone condition (see FIG. 1) which emulates the re-experiencing symptom of human PTSD patients. Thus, while the candidate compound can probably help many PTSD patients, it is least suited to those patients that suffer re-experiencing to a significant degree. Statistical analysis was as in Example 4, Results were significant ($p<0.05$).

Example 10

Analysis of 30% Amelioration of Symptoms Using with Companion and Hyper Arousal Conditions Analyzed as a Pool Using the same 30% improvement threshold described in example 7, the percentage of saline-treated and candidate compound-treated rats that improved (light grey portion of bar) or did not improve (dark grey portion of bar) as a result of treatment under with companion and hyper conditions was analyzed as a pool. Results are summarized graphically in FIG. 8. In this case, the candidate compound nearly tripled the number of animals experiencing a 30% improvement indicating that it has potential utility in ameliorating symptoms in human PTSD patients that suffer primarily from amplified startle response and/or impaired social interaction. Statistical analysis was as in Example 4, Results were significant ($p<0.05$).

Example 11

Remission under with Companion Conditions

Figure 9:
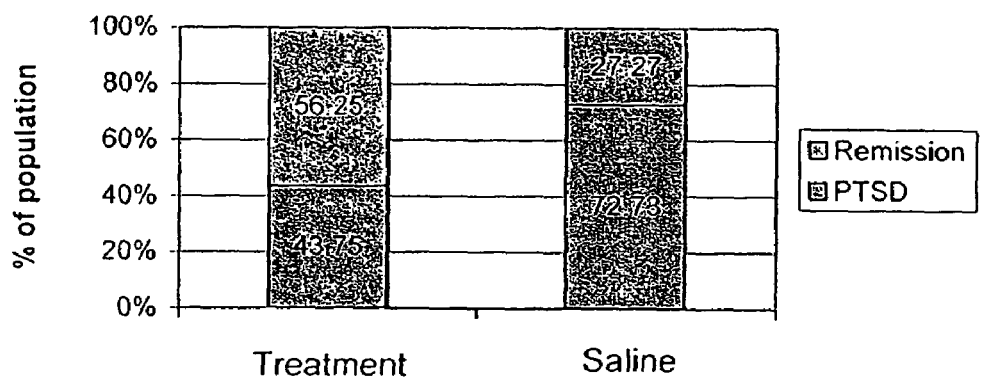
FIG. 9 is a split bar graph illustrating the breakdown of the population of saline-(n=11) and candidate compound-treated (n=16) rats that went into remission in avoidance "with companion" condition. "Remission" rats were PTSD rats whose freezing responses were restored to within the range of baseline values after treatment.

While the 30% amelioration of symptoms criteria employed in examples 7 through 10 is a useful predictor, an ideal candidate compound would induce remission in a significant number of cases. In order to assess the likelihood of remission as an outcome of treatment, "in remission" rats were defined as those maladapted (PTSD) rats whose freezing responses under defined conditions were restored to the normal range of baseline values as a result of treatment. FIG. 9 summarizes graphically the percentage of rats that were in remission (light grey portion of bar) or not in remission (dark grey portion of bar) as a result of treatment under with companion conditions. Under with companion conditions, the candidate compound more than doubled the percentage of animals in remission as a result of treatment indicating that it has potential utility in inducing remission in human PTSD patients that suffer primarily from impaired social interaction. Statistical analysis was as in Example 4, Results were significant ($p<0.05$).

Example 13

Remission under Hyper Arousal Conditions

Figure 10:
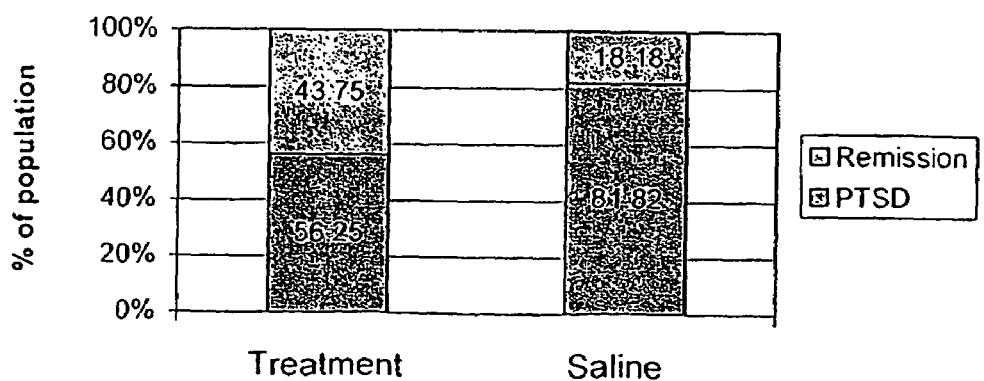
FIG. 10 is a split bar graph illustrating the breakdown of the population of saline-(n=11) and candidate compound-treated (n=16) rats that went into remission in "hyper-arousal" condition. "Remission" is as defined in the legend of FIG. 9.

Using the same remission criteria defined in example 12, data collected under hyperarousal conditions were analyzed. FIG. 10 summarizes graphically the percentage of rats that were in remission (light grey portion of bar) or not in remission (dark grey portion of bar) as a result of treatment under hyper arousal conditions. Under hyper arousal conditions, the candidate compound more than doubled the percentage of animals in remission as a result of treatment indicating that it has potential utility in inducing remission in human PTSD patients that suffer primarily from exaggerated startle response. Statistical analysis was as in Example 4, Results were significant (p<0.05).

Example 14

Remission under Alone Conditions

Figure 11:
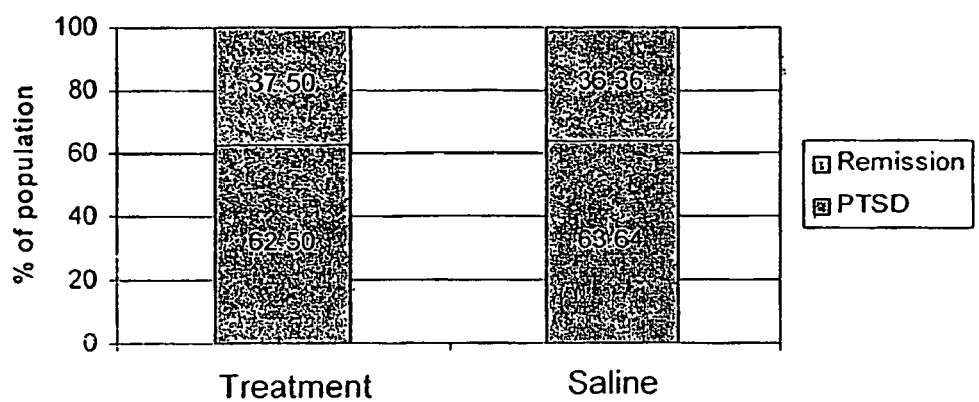
FIG. 11 is a split bar graph illustrating the breakdown of the population of saline-(n=11) and candidate compound-treated (n=16) rats that went into remission in "alone" condition. "Remission" is as defined in the legend of FIG. 9.

Using the same remission criteria defined in example 12, data collected under alone conditions were analyzed. FIG. 11 summarizes graphically the percentage of rats that were in remission (light grey portion of bar) or not in remission (dark grey portion of bar) as a result of treatment under alone conditions. Under alone conditions, the candidate compound had virtually no effect relative to saline treatment indicating that it little or no potential utility in inducing remission in human PTSD patients that suffer primarily from re-experiencing. These results confirm those presented in FIG. 1 and described hereinabove. Statistical analysis was as in Example 4, Results were significant (p<0.05).

Example 15

Theoretical Basis of the Model

Figure 13:
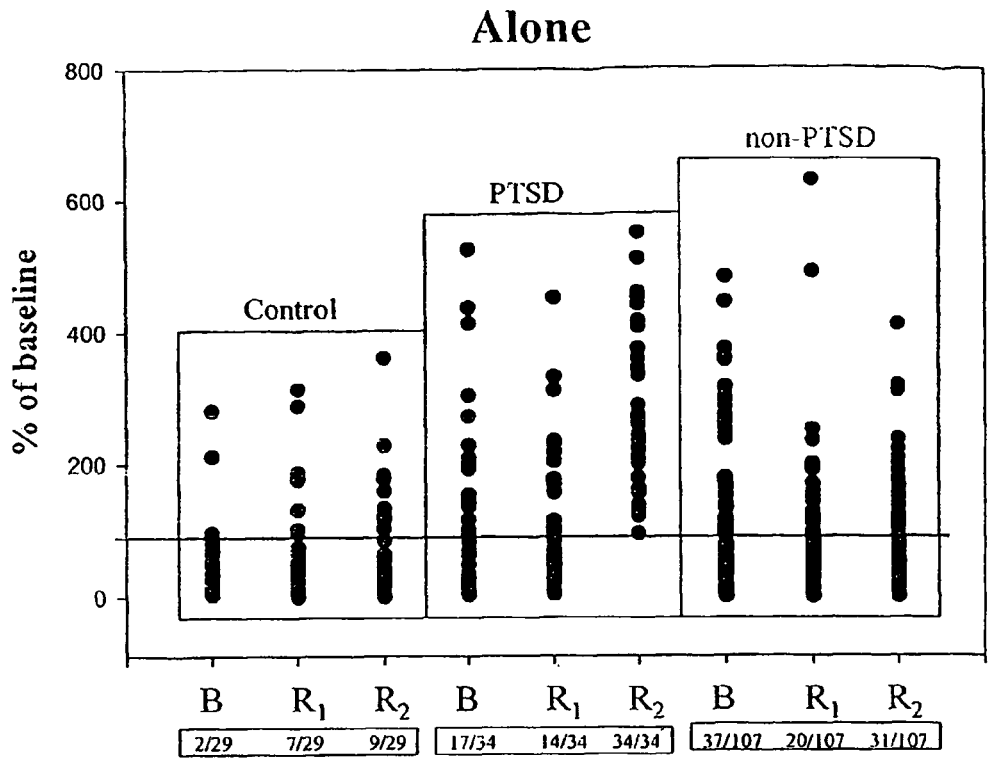
FIG. 13 is a vertical scatter plot of freeze times for individual rats in control, PTSD and non-PTSD groups as observed in the "alone" condition as a % of baseline. E indicates first exposure to trauma (item 3 in FIG. 12), R1 indicates first exposure to a trauma like stimulus (item 4 in FIG. 12), R2 indicates second exposure to a trauma like stimulus (item 5 in FIG. 12). The horizontal line across the panel indicates the upper limit of mean baseline values as collected from all participants in the study normalized to 100%.
Figure 14:
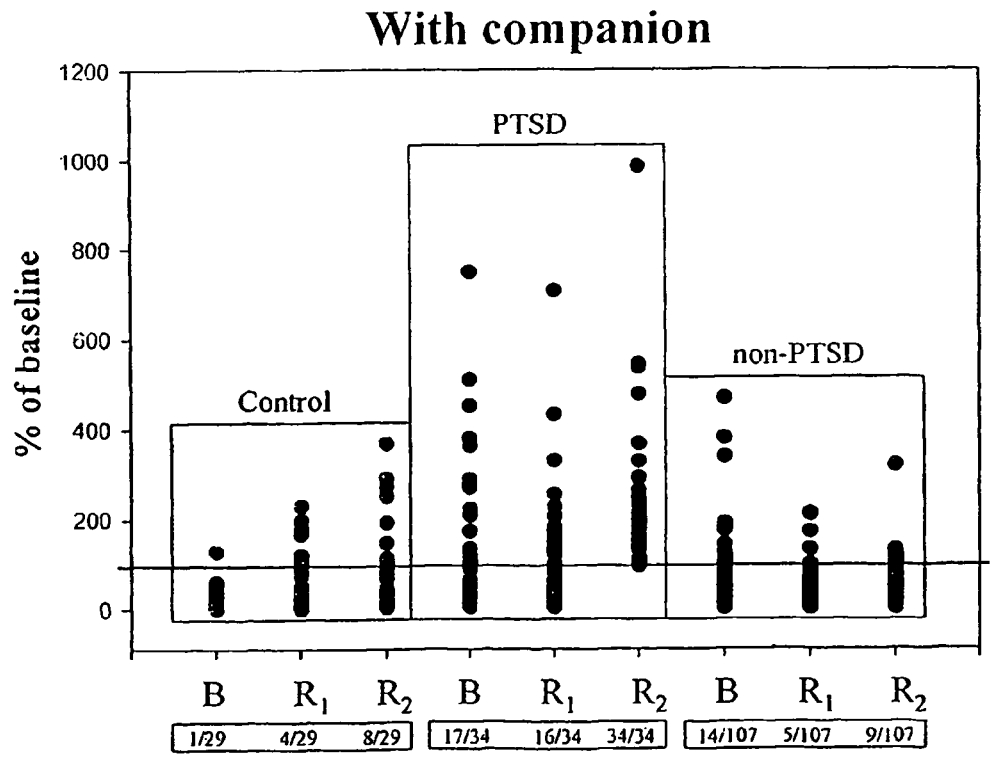
FIG. 14 is similar to FIG. 13 in all respects except that data is from the "with companion" condition.
Figure 15:
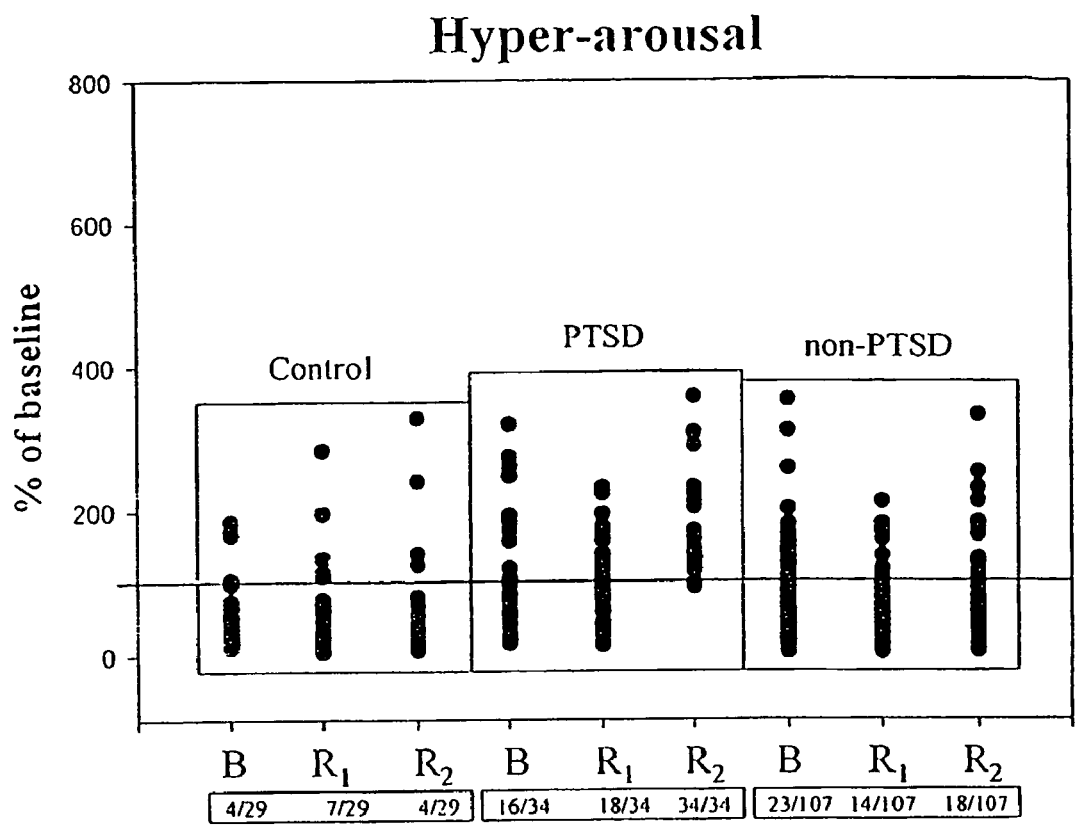
FIG. 15 is similar to FIG. 13 in all respects except that data is from the "hyperarousal" condition.

FIGS. 13-15 are vertical scatter plots of freeze times for individual rats in control, PTSD and non-PTSD groups as observed in the "alone", "with companion" and "hyperarousal conditions respectively. In each case, data are presented as a % of baseline. E indicates first exposure to trauma with regard to the PTSD and non-PTSD groups and exposure to clean litter for the control groups (item 3 in FIG. 12). R1 indicates a first exposure to a trauma like stimulus (item 4 in FIG. 12). R2 indicates a second exposure to a trauma like stimulus (item 5 in FIG. 12). The upper horizontal line across each panel indicates the upper limit of mean baseline values as collected from all participants in the study normalized to 100%. The fraction below each vertical bar indicates individuals over baseline/total individuals. Exposure of control rats to the trauma related stimulus (R1) produced freezing time results within the basal range. Re-exposure of control rats to the trauma related stimulus (R2) produced freezing time results which were primarily within the basal range although a few individuals surpassed basal levels. In sharp contrast re-exposure of PTSD rats to the trauma related stimulus (R2) produced freezing time results which were primarily above the basal range.

Example 16

Establishing a Link between Behavioral Parameters and Biological Parameters

In order to investigate the physiologic basis of the observed behavioral responses, mRNA was isolated from brain tissue of PTSD and control rats as detailed hereinabove in Materials and Methods. These rats received no drugs.

Because Koks et al. have demonstrated the involvement of Wolframin in a normal fear response (Neuroscience Letters 322 (2002) 116-120), expression levels of that gene were characterized in amygdala and CA1 portions of the brain in PTSD and non PTSD rats.

Because Sigma-1 receptors have been shown to play an important role in antidepressive effects and in conditioned fear stress (Nippon Shinkei Seishin Yakurigaku Zasshi 23(5): 187-196 *REVIEW Japanese*; Nippon Yakurigaku Zasshi 114 (1):43-49 *REVIEW Japanese*; and Neuroreport 9(13):3069-3073) expression levels of the Sigma 1 receptor gene were characterized in amygdala and CA1 portions of the brain in PTSD and non PTSD rats.

Figure 16:
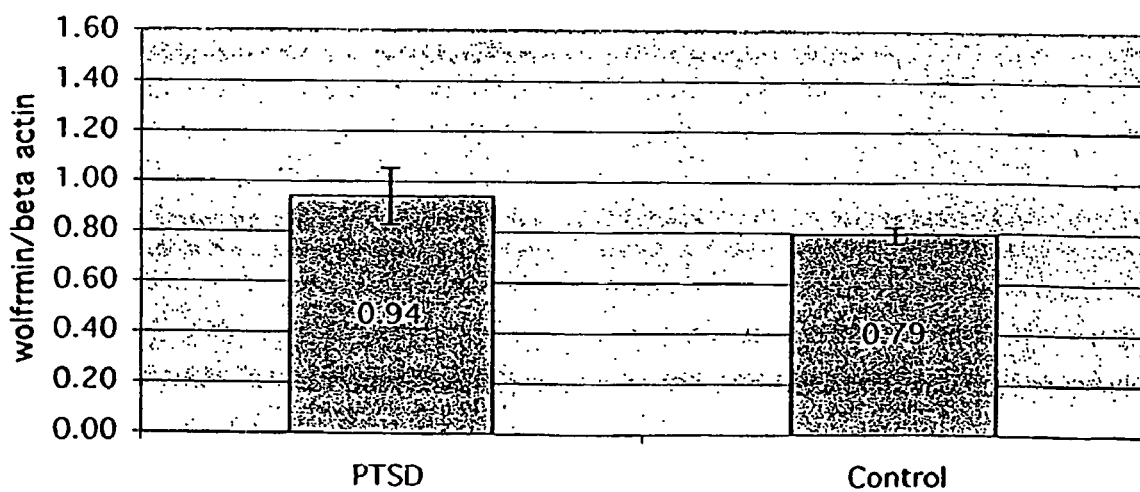
FIG. 16 is a bar graph illustrating expression levels of Wolframin mRNA relative to beta actin in the amygdala in control and PTSD rats as indicated.
Figure 17:
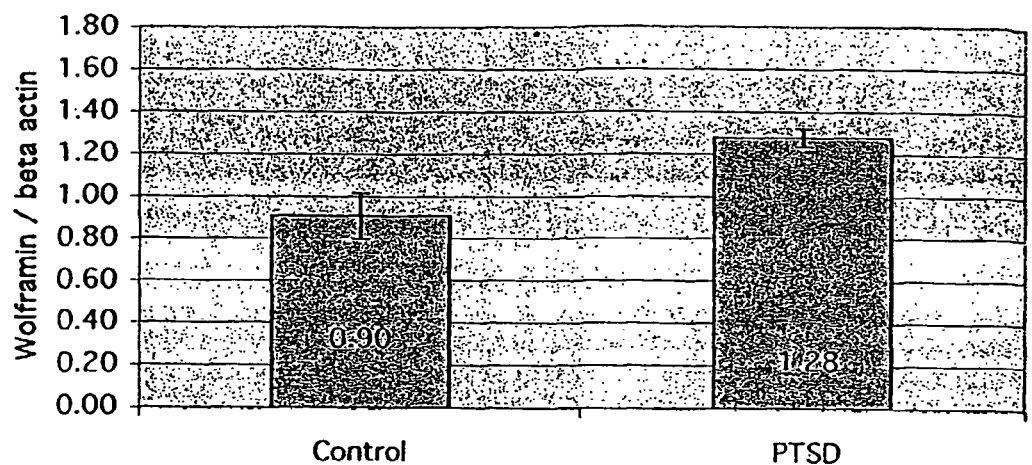
FIG. 17 is a bar graph illustrating expression levels of Wolframin mRNA relative to beta actin in the CA1 in control and PTSD rats as indicated.
Figure 18:
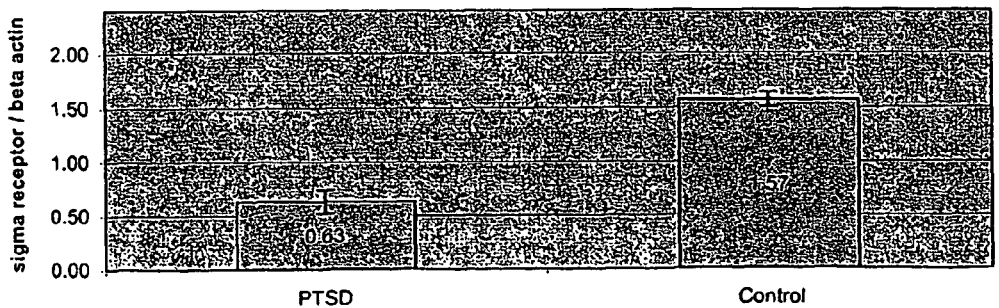
FIG. 18 is a bar graph illustrating expression levels of Sigma Receptor mRNA relative to beta actin in the amygdala in control and PTSD rats as indicated.
Figure 19:
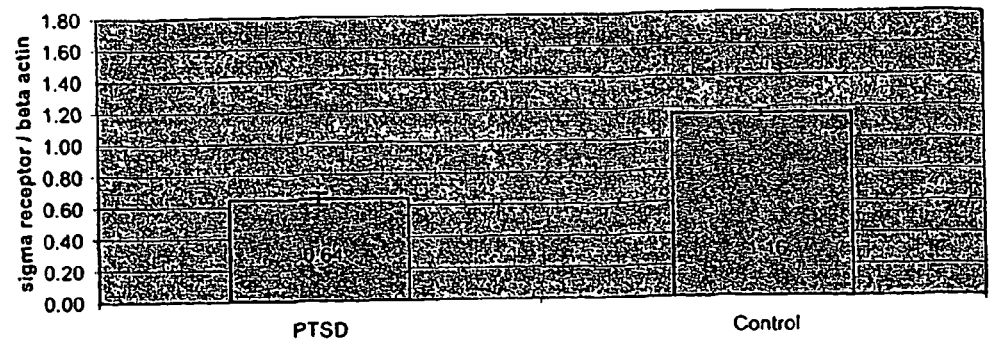
FIG. 19 is a bar graph illustrating expression levels of Sigma Receptor mRNA relative to beta actin in the CA1 in control and PTSD rats as indicated.

FIGS. 16 and 17 are bar graphs illustrating expression levels of Wolframin mRNA relative to beta actin in control and PTSD rats in the amygdala and CA1 respectively. Maladapted PTSD rats produced by the disclosed methods exhibited significantly higher Wolframin levels in both the amygdala and CA1. FIGS. 18 and 19 are bar graphs illustrating expression levels of Sigma Receptor 1 mRNA relative to beta actin in control and PTSD rats in the amygdala and CA1 respectively. Maladapted PTSD rats produced by the disclosed methods exhibited significantly lower Sigma Receptor 1 levels in both the amygdala and CA1.

These results indicate, for the first time, that there is a concrete physiologic mechanism underlying the behavioral aberrations associated with PTSD. Although the specific examples of biological parameters presented here require invasive brain biopsies, they serve to establish the importance of the disclosed animal model in identifying and characterizing biological markers effected by PTSD in general. Thus, the disclosed model may find utility in validating, for example, PTSD markers in the blood circulation.

Example 17

Drug Screening Based Upon Biological Parameters Alone

In order to demonstrate that biological data, such as Wolframin or Sigma 1 receptor expression levels, could be used as a substitute for behavioral data in identifying maladapted PTSD individuals, confidence interval were calculated using the same raw data employed to generate FIGS. 16 and 17 (Wolframin) and 18 and 19 (Sigma 1 receptor). Table 6 presents the confidence intervals for Wolframin expression in Amygdala and CA1 brain biopsies for both PTSD and control animals. Table 7 presents the confidence intervals for Sigma 1 receptor expression in Amygdala and CA1 brain biopsies for both PTSD and control animals.

TABLE 6

Confidence intervals for brain Wolframin levels

| | | | 95% Confidence Interval for Mean | |
|---|---|---|---|---|
| | | Mean | Lower Bound | Upper bound |
| Amygdala | PTSD | 0.943 | 0.46387 | 1.42213 |
| Amygdala | Control | 0.794 | 0.65785 | 0.93015 |
| CA1 | PTSD | 1.28 | 1.1417 | 1.4143 |
| CA1 - | Control | 0.9048 | 0.66628 | 1.14332 |

TABLE 7

Confidence intervals for brain Sigma receptor 1 levels

| | | | 95% Confidence Interval for Mean | |
|---|---|---|---|---|
| | | Mean | Lower Bound | Upper bound |
| Amygdala | PTSD | 0.63367 | 0.16398 | 1.10335 |
| Amygdala | Control | 1.54733 | 1.26327 | 1.8314 |
| CA1 | PTSD | 0.64425 | 0.52073 | 0.76777 |
| CA1 - | Control | 1.157676 | 1.04921 | 1.26613 |

These results indicate that data from either of these biological parameters (and presumably additional biological parameters which remain to be identified) could be used as a substitute for behavioral data in assessing the efficacy of a candidate compound in ameliorating the effects of PTSD.

This substitution would have to be in the context of an established, well defined behavioral model where significant data on the expected number of maladapted PTSD like individuals from a population is available. Such a behavioral model is presented hereinabove. An example of one statistical method is presented hereinabove, although other theoretically similar statistical a methods are within the scope of the invention.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

REFERENCES

American Psychiatric Association, Diagnostic and Statistical Manual of Mental Disorders, 4$^{th}$ edn (DSM-IV) (American Psychiatric Press: Washington, D.C., 1994).

Brady K T, Sonne S C, Roberts J M, Sertraline treatment of comorbid posttraumatic stress disorder and alcohol dependence. J Clin Psychiatry (1995) 56:502-5.

Kessler R C, Sonnega A, Bromet E J et al, Posttraumatic stress disorder in the National Comorbidity Survey, Arch Gen Psychiatry (1995) 52:1048-60.

Kosten T R, Ziedonis D M, Substance abuse and schizophrenia: editors' introduction, Schiz Bull (1997):23(2):181-6.

Pitman R K, Orr S P, Twenty-four hour urinary cortisol and catecholamin excretion in combat-related posttraumatic stress disorder, Biol Psychiatry (1990) 15:27(2)245-7.

Stein D J, Seedat S, Van der Linder, Kaminer D, Pharmacotherapy of post-traumatic stress disorder In "Post-traumatic Stress Disorder" Ed Natt D, Davidson J, Zohar J, Martin Dunitz Ltd. 2000 London. 2000 pp 131-46.

Yehuda R, Giller, E L, Southwick S M, Lowy M T, Mason J W, Hypothalamic pituitary-adrenal dysfunction in post-traumatic-stress-disorder, Biol Psychiatry (1991) 30:(10) 1031-48.

Yehuda R, Southwick S M, Nussbaum G, Wahby V, Giller E L Jr, Mason J W, Low urinary cortisol excretion in patients with posttraumatic stress disorder. J Nerv Ment Dis (1990) 178(6):366-9.

Young E A, Kwak S P, Kottak J, Negative feedback regulation following administration of chronic exogenous corticosterone, J Neuroendocrinol (1995) 7(1):37-45.

What is claimed:

1. A method for producing a subset of maladapted non-human mammals characterized by post-traumatic stress disorder (PTSD)-like behavior from a group of non-human mammals by behavioral conditioning, the method comprising: (a) determining an individual baseline behavioral level and at least one biological parameter selected from the group consisting of a Wolframin level and a Sigma 1 receptor level for each one of an individual non-human mammal in the group after a period of habituation to a defined set of conditions; (b) exposing each one of said individual non-human mammal in the group to a trauma event and further determining an individual posttraumatic event behavioral level and the level of said at least one biological parameter for each of said individual non-human mammal; (c) re-exposing each of said individual non-human mammal in the group to a trauma related event and further determining an individual post trauma related event behavioral level and the level of said at least one biological parameter for each individual non-human mammal; (d) evaluating said individual post trauma related event behavioral level and the level of said at least one biological parameter for each individual non-human mammal with respect to at least one baseline value according to a predetermined rule in order to determine which of said individual non-human mammal in the group belong to the subset of maladapted non-human mammals characterized by PTSD-like behavior.

2. A method for producing a subset of maladapted non-human animals characterized by post-traumatic stress disorder (PTSD)-like behavior from a group of non-human mammals by behavioral conditioning, the method comprising: (a) determining an individual baseline behavioral level for each one of an individual non-human mammal in the group after a period of habituation to a defined set of conditions; (b) exposing each one of said individual non-human mammal in the group to a trauma event at least 21 days following the start of habituation and further determining an individual posttraumatic event behavioral level for each of said individual non-human mammal; (c) re-exposing each of said individual non-human mammal in the group to a trauma related event at least 7 days following said exposure to a trauma event and further determining an individual post trauma related event behavioral level for each individual non-human mammal; (d) evaluating said individual post trauma related event behavioral level for each individual animal with respect to at least one baseline value according to a predetermined rule in order to determine which of said individual non-human mammal in the group belong to the subset of maladapted non-human mammals characterized by PTSD-like behavior.

3. The method of claim 2, wherein said determining an individual baseline behavioral level, said further determining an individual post traumatic event behavioral level, further determining an individual post trauma related event behavioral level are each independently accomplished by analysis of videotapes of a defined behavior of said individual non-human mammal under controlled conditions.

4. The method of claim 3, further comprising at least one repetition of said re-exposing each of said individual non-human mammal in the group to a trauma related event and of said further determining an individual post trauma related event behavioral level for each individual non-human mammal.

5. The method of claim 4, wherein said at least one repetition of said re-exposing of said individual non-human mammal to a trauma related event occurs between 14 days and 90 days following said exposing to a trauma event.

6. The method of claim 5, wherein said at least one repetition of said re-exposing of said individual non-human mammal to a trauma related event occurs 23 days following said exposing to a trauma event.

7. The method of claim 2, wherein said exposing of (b) of each one of said individual non-human mammal to a trauma event occurs 23 days following the start of habituation and said re-exposing of (c) of each of said individual non-human mammal to a trauma related event occurs 7 days following said exposure to a trauma event.

8. A method for screening a candidate compound for PTSD treatment, the method comprising: (a) producing a subset of individually evaluated maladapted non-human mammals characterized by PTSD like behavior from a group of non-human mammals wherein an individual in said subset is correlatable to a corresponding individual behavioral profile; (b) identifying each of said individuals in said subset of individually evaluated maladapted non-human mammals characterized by PTSD like behavior; (c) administering a candidate compound to at least a portion of said individuals in said subset; (d) determining an effect of said candidate compound on each of said individuals in said at least a portion of said subset with respect to said corresponding individual behavioral profile.

9. The method of claim 8, further comprising measuring at least one biological parameter in each of said individually evaluated maladapted non-human mammals.

10. The method of claim 9, wherein said at least one biological parameter is selected from the group consisting of a Wolframin level and a Sigma 1 receptor level.

11. The method of claim 8, further comprising applying an accepted statistical analysis to a pool of data pertaining to said effect of said candidate compound on each of said individuals in said at least a portion of said subset with respect to said corresponding individual behavioral profile.

12. The method of claim 8, further comprising administering a control compound to at least a portion of said individuals in said subset.

13. The method of claim 12, wherein said control compound includes at least one compound selected from the group consisting of a negative control compound and a compound with a previously characterized efficacy in treating PTSD.

14. The method of claim 8, wherein the method is performed as iterated and wherein the treatment is a therapeutic treatment.

15. The method of claim 8, wherein the treatment is a prophylactic treatment.

16. A method for screening a candidate compound for prophylactic PTSD treatment, the method comprising: (a) establishing a method for producing a subset of maladapted non-human mammals characterized by PTSD like behavior from a group of non-human mammals by behavioral conditioning; (b) employing statistical methods to determine a confidence interval for a relative size of said subset of maladapted non-human mammals characterized by PTSD like behavior with respect to a size of said group of non-human mammals; (c) administering the candidate compound to a subsequent group of animals subjected to said method for producing a subsequent subset of maladapted non-human mammals characterized by PTSD like behavior; and (d) determining whether a relative size of said subsequent subset of maladapted non-human mammals characterized by PTSD like behavior with respect to a size of said subsequent group of non-human mammals falls within said confidence interval.

17. A method for screening a candidate compound for PTSD treatment, the method comprising: (a) establishing a method for producing a subset of maladapted PTSD like non-human mammals from a group of non-human mammals by behavioral conditioning; (b) measuring at least one biological parameter for each non-human mammal in said subset of maladapted PTSD like non-human non-human mammals; (c) employing statistical methods to: (i) determine a first confidence interval for a relative size of said subset of maladapted PTSD like non-human non-human mammals with respect to a size of said group of non-human mammals; (ii) determine a second confidence interval for said at least one biological parameter for said subset of maladapted PTSD like non-human mammals; (d) administering the candidate compound to a subsequent group of non-human mammals subjected to said method for producing a subsequent subset of maladapted non-human mammals characterized by PTSD like behavior; and (e) determining whether a relative size of a subset of said subsequent group of non-human mammals characterized by a value for said at least one biological parameter which falls within said second confidence interval falls within said first confidence interval; and (f) concluding that: (i) the candidate compound is effective in ameliorating PTSD if said relative size of said subset of said subsequent group of non-human mammals characterized by a value for said at least one biological parameter which falls within said second confidence interval is below a lower bound of said first confidence interval; or (ii) the candidate compound is not effective in ameliorating PTSD if said relative size of said subset of said subsequent group of non-human mammals characterized by a value for said at least one biological parameter which falls within said second confidence interval is above a lower bound of said first confidence interval.

18. The method of claim 17, wherein said at least one biological parameter includes at least one item selected from the group consisting of a Wolframin level and a Sigma 1 receptor level.

* * * * *

UNITED STATES PATENT AND TRADEMARK OFFICE
CERTIFICATE OF CORRECTION

PATENT NO.        : 7,652,191 B2  
APPLICATION NO.   : 10/549596  
DATED             : January 26, 2010  
INVENTOR(S)       : Yadid et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 267 days.

Signed and Sealed this

Twenty-third Day of November, 2010

David J. Kappos  
*Director of the United States Patent and Trademark Office*